(12) United States Patent
Park et al.

(10) Patent No.: US 8,962,258 B2
(45) Date of Patent: Feb. 24, 2015

(54) APPARATUS AND METHOD FOR MULTIPLE IMMUNOASSAYS ON A CHIP

(75) Inventors: Je-Kyun Park, Daejeon (KR); MinSeok Kim, Daejeon (KR); Eun Sook Lee, Seoul (KR); Sun-Young Kong, Goyang-si (KR); Solm Kwon, Paju-si (KR)

(73) Assignees: Korea Advanced Institute of Science and Technology, Daejon (KR); National Cancer Center, Goyang-si, Gyeonggi-do (KR)

( * ) Notice: Subject to any disclaimer, the term of this patent is extended or adjusted under 35 U.S.C. 154(b) by 10 days.

(21) Appl. No.: 13/060,402

(22) PCT Filed: Aug. 29, 2008

(86) PCT No.: PCT/KR2008/005088
§ 371 (c)(1),
(2), (4) Date: Feb. 23, 2011

(87) PCT Pub. No.: WO2010/024485
PCT Pub. Date: Mar. 4, 2010

(65) Prior Publication Data
US 2011/0152121 A1    Jun. 23, 2011

(51) Int. Cl.
*G01N 33/53* (2006.01)
*G01N 1/31* (2006.01)
(Continued)

(52) U.S. Cl.
CPC ............... *G01N 1/312* (2013.01); *B01L 3/502* (2013.01); *G01N 1/28* (2013.01); *G01N 1/2806* (2013.01);
(Continued)

(58) Field of Classification Search
USPC ................... 422/417, 68.1, 81, 82.05, 82.08, 422/502–505, 536, 554, 559; 435/7.1, 7.2, 435/7.21, 7.23, 960, 973, 283.1, 286.5, 435/287.1–287.3, 287.9, 288.3, 288.4, 435/288.5
See application file for complete search history.

(56) References Cited

U.S. PATENT DOCUMENTS 7,883,669 B2 * 2/2011 Sun et al. ...................... 422/504
2003/0138829 A1 7/2003 Unger et al.
(Continued)

OTHER PUBLICATIONS

V. J. Sieben, et al., FISH and chips: chromosomal analysis on microfluidic platforms, IET Nanobiotechnol. vol. 1 (3):27-35 (Jun. 2007).
(Continued)

*Primary Examiner* — Melanie Y Brown
*Assistant Examiner* — Erik B Crawford
(74) *Attorney, Agent, or Firm* — Lucas & Mercanti, LLP

(57) ABSTRACT

Provided are a multiple immunoassay apparatus on a chip in which a structure comprising multiple microfluidic channels is associated with a tissue sample, which allows immunohistochemical reactions to be conducted therein, to examine various markers specific for certain diseases, and a method for performing multiple immunoassays using the same. The multiple immunoassay apparatus comprises: at least one antibody-introducing unit through which at least one antibody is introduced into the apparatus; at least one reaction unit in which the antibody reacts with a sample in an immunohistochemical pattern; and at least one fluid outlet through which a fluid including the antibody is discharged outside the apparatus.

17 Claims, 13 Drawing Sheets

(51) Int. Cl.
  *B01L 3/00* (2006.01)
  *G01N 1/28* (2006.01)
  *G01N 1/30* (2006.01)

(52) U.S. Cl.
  CPC ............... *G01N 1/2813* (2013.01); *G01N 1/30* (2013.01); *G01N 33/5302* (2013.01); *B01L 2300/0816* (2013.01); *B01L 2300/0861* (2013.01); *B01L 2300/0877* (2013.01); *B01L 2300/0883* (2013.01); *Y10S 435/96* (2013.01); *Y10S 435/973* (2013.01)
  USPC ........... 435/7.1; 435/960; 435/7.2; 435/7.21; 435/7.23; 435/973; 435/283.1; 435/286.5; 435/287.1; 435/287.2; 435/287.3; 435/287.9; 435/288.3; 435/288.4; 435/288.5; 422/68.1; 422/81; 422/82.05; 422/501; 422/536

(56) References Cited

U.S. PATENT DOCUMENTS

| | | |
|---|---|---|
| 2004/0209354 A1 | 10/2004 | Mathies et al. |
| 2007/0090732 A1* | 4/2007 | Langseth et al. ............... 310/800 |
| 2007/0248958 A1* | 10/2007 | Jovanovich et al. ............. 435/6 |
| 2008/0318334 A1* | 12/2008 | Robotti ........................ 436/161 |

OTHER PUBLICATIONS

S. B. Cheng, et al., Development of a multichannel microfluidic analysis system employing affinity capillary electrophoresis for immunoassay, Anal. Chem. vol. 73(7): 1472-1479 (2001).

\* cited by examiner

APPARATUS AND METHOD FOR MULTIPLE IMMUNOASSAYS ON A CHIP

CROSS-REFERENCE TO RELATED APPLICATIONS

This application is a 371 of PCT/KR2008/005088 filed on Aug. 29, 2008, the content of which is incorporated herein by reference.

TECHNICAL FIELD

The present invention relates to a multiple immunoassay apparatus, such as fluorescence in situ hybridization of biosamples including cells and tissues based on immunohistochemistry. More particularly, the present invention relates to a multiple immunoassay apparatus in conjunction with a Lab-on-a-chip technology which is useful in detecting the presence of enzymes, tumor markers and prognosis markers and determining whether a tumor is carcinoma or sarcoma, or is benign or malignant, and which can conduct in a simple manner biological experiments requiring extensive time and labor.

BACKGROUND ART

Morphological observations of samples from the lesions of patients are important for the accurate diagnosis, appropriate treatment, and study of diseases. Of these, immunohistochemical staining is a highly sensitive and specific biopsy process which finds a broad spectrum of applications in the research field related to diagnosis.

The many advances of the last two decades in the immunohistochemical staining field have introduced staining methods capable of quickly reading out results, allow for retrospective studies with paraffin slides, and have developed thousands of readily usable antibodies for detecting antigens.

Immunohistochemistry having such advantages is now recognized as a fundamental and effective diagnostic method, but requires an examination of various markers of cancer to make an accurate diagnosis of cancer and to conduct appropriate chemotherapy and molecular therapy for the patients. However, limited tissue samples, low yields involved with preparing paraffin blocks from tissue samples, and economic and time burdens on patients make it clinically difficult to make an examination of various markers.

DISCLOSURE

Technical Problem

Accordingly, the present invention has been made keeping in mind the above problems occurring in the prior art, and an object of the present invention is to provide a multiple immunoassay apparatus on a chip in which a structure comprising multiple microfluidic channels is associated with a tissue sample, which allows immunohistochemical reactions to be conducted therein, to examine various markers specific for certain diseases, and to provide a method for performing multiple immunoassays using the same.

Technical Solution

In order to accomplish the above objects, the present invention provides a multiple immunoassay apparatus, comprising: at least one antibody-introducing unit through which at least one antibody is introduced into the apparatus; at least one reaction unit in which the antibody reacts with a sample in an immunohistochemical pattern; and at least one fluid outlet through which a fluid including the antibody is discharged outside the apparatus.

In a modification of the apparatus, the antibody-introducing unit, the reaction unit and the fluid outlet are interconnected with each other through channels.

In another modification, the apparatus further comprises a pressure provider for providing a pressure to control a flow rate of fluid within the channels.

In this modification, the pressure provider is a hydraulic or pneumatic device.

In a further modification, the apparatus further comprises at least one fluid controller for controlling fluid flows, the fluid controller being connected with the antibody-loading unit, the reaction unit and the fluid outlet via channels.

In yet a further modification, the apparatus further comprises an electric heater for controlling a temperature of the apparatus, the electric heater being located on a lower side of the apparatus to establish a condition optimal for a reaction between an antibody and a sample.

In yet another modification of the apparatus, the number of reaction units is the same as the number of the antibody-introducing unit.

In still another modification, the apparatus further comprises a transparent cover for covering the apparatus to prevent the fluid from evaporating.

In still a further modification, the apparatus further comprises at least one reagent-introducing unit through which a reagent necessary for an immunoassay is introduced.

In still yet another modification, the apparatus further comprises a pressurizing unit for compressing the reaction unit to promote reactions between the antibody, the reaction and the sample.

In this modification, the pressurizing unit is operated in a bolt-nut manner, in a spring compressing manner, or in a balance weight manner.

In still yet a further modification of the apparatus, the reaction unit is formed in a zigzag pattern.

In an additional modification of the apparatus, the antibody and the reagent react with the sample while flowing through the reaction unit.

In another additional modification of the apparatus, the sample is a tissue sample or a cell sample.

In a yet additional modification, the apparatus has a lab-on-a-chip structure in which the antibody-introducing unit, the reagent-loading unit, the reaction unit and the fluid outlet are all established on a chip.

In a further additional modification of the apparatus, the reaction unit has a width of 3 cm or smaller.

In accordance with another aspect thereof, the present invention provides a method for performing multiple immunoassays using the apparatus, comprising: loading one or more antibodies into respective antibody-loading units; providing a pressure to move fluids of the antibodies to respective reaction units; allowing the antibodies to react with a sample including a tissue slice sample to examine markers specific for diseases; and discharging the fluids through fluid outlets connected to the reaction units.

In a modification thereof, the method further comprises loading reagents to respective reagent-introducing units prior to, subsequently to or simultaneously with the loading of the antibodies.

In another modification thereof, the method further comprises controlling flows of the fluids including the antibodies and the reagents to the sample after the provision of pressure.

In a further modification of the method, the pressure is provided using a hydraulic or pneumatic device.

In still a further modification thereof, the method further comprises compressing the reaction units to promote the reaction between the antibodies and the sample.

Advantageous Effects

As described above, the apparatus and the method for performing multiple immunoassays in accordance with the present invention can reduce the consumption of expensive antibodies to one tenth that of conventional apparatuses and methods.

In addition, the apparatus and method of the present invention allows various markers to be detected on even one tissue slice sample, thus surmounting the low yield of immunohistochemistry, and can secure medical information on various tissues of a cancer patient within a short period of time, ensuring accurate diagnosis leading to optimal chemo- and molecular therapy.

Further, the apparatus and method of the present invention can obtain information on the prognosis of patients which is greatly helpful in choosing therapeutic methods and reduces biochemical and medical examinations in terms of time and cost, thus allowing medical treatments to be rapidly applied to patients with a great reduction in financial burden of the patients.

BEST MODE

In accordance with an aspect thereof, the present invention provides a multiple immunoassay apparatus, comprising: at least one antibody-introducing unit through which at least one antibody is introduced into the apparatus; at least one reaction unit in which the antibody reacts with a sample in an immunohistochemical pattern; and at least one fluid outlet through which a fluid including the antibody is discharged outside the apparatus.

In accordance with another aspect thereof, the present invention provides a method for performing multiple immunoassays, comprising: loading one or more antibodies into respective antibody-loading units; providing pressure to move fluids of the antibodies to respective reaction units; allowing the antibodies to react with a sample including a tissue slice sample to examine markers specific for diseases and discharging the fluids through fluid outlets connected to the reaction units.

Mode for Invention

Hereinafter, embodiments of the present invention will be described in detail with reference to the attached drawings.

First Embodiment

Figure 1:
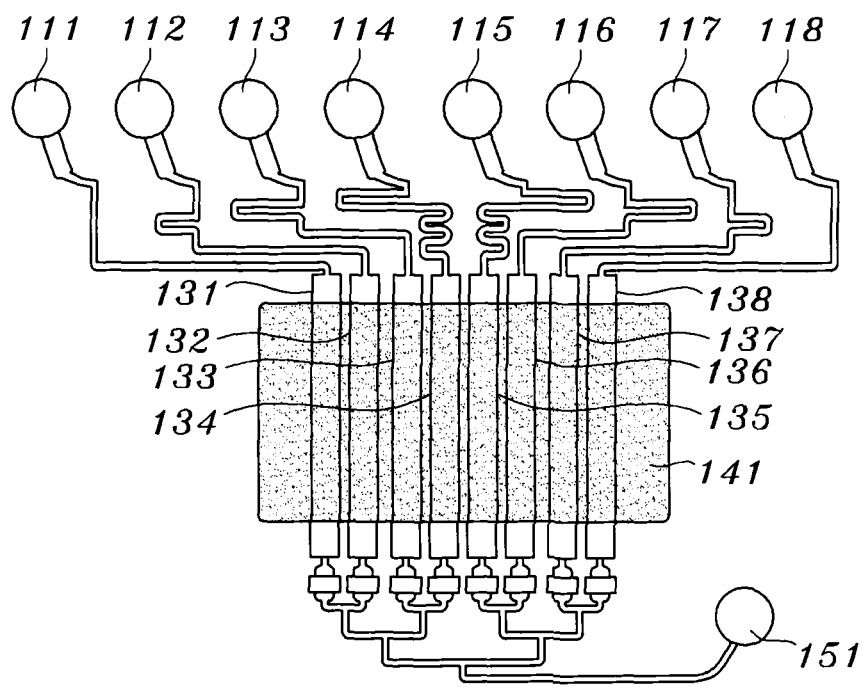
FIGS. 1 and 2 are, respectively, structural and cross-sectional views of a multiple immunoassay apparatus in accordance with a first embodiment of the present invention.
Figure 2:
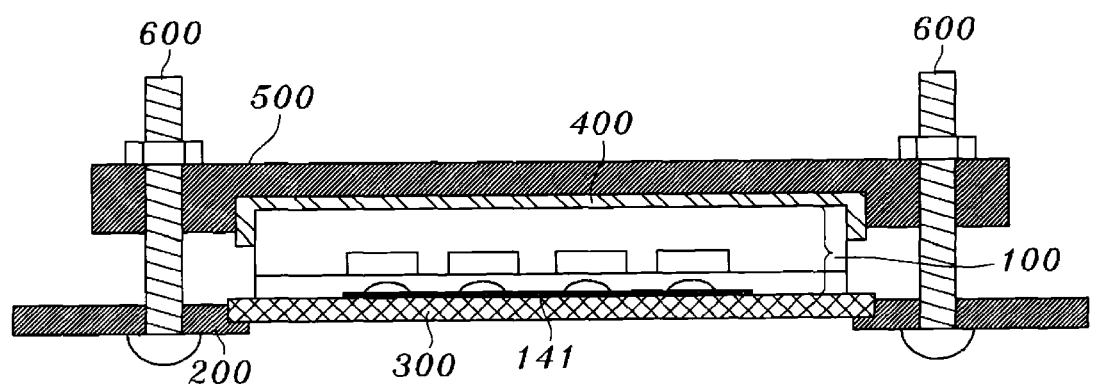

With reference to FIGS. 1 and 2, a multiple immunoassay apparatus on a chip in accordance with a first embodiment of the present invention is shown in a structural diagram and a cross sectional view, respectively. The apparatus according to the first embodiment of the present invention comprises at least one antibody loading unit, at least one reaction unit and at least one fluid outlet.

First, operation and functions of the multiple immunoassay apparatus will be described, consulting these figures.

The present invention may be applied to various biological assays, such as fluorescence in situ hybridization (FISH), and immunohistochemistry is now delineated as a representative example. As shown in FIG. 1, the apparatus comprises eight antibody loading units 111~118, numbered one to eight, through which primary antibodies necessary for immunohistochemistry are introduced. The processes of the immunohistochemistry prior to the reaction of the primary antibodies may be conducted in a typical manner.

Communicating with the reaction unit via channels, there are as many antibody loading units as there are channels. Each antibody loading unit may further comprise a fluid controller for controlling a flow of antibody by opening or closing the channels. The fluid controller and the antibody loading unit may be increased or decreased in number if necessary. In this embodiment, eight antibody loading units are given. A fluid containing a primary antibody suitable for use in immunohistochemistry is loaded on the antibody loading unit. In the first embodiment, 8 reaction unit channels and are provided, and the corresponding 8 antibody loading units, that is, a first antibody loading unit 111 to an eighth antibody loading unit 118, are provided as well.

In addition, the apparatus in accordance with the first embodiment of the present invention may further comprise a pressure provider, connected to the channel, for controlling the flow rate of the fluid in the channel. As the pressure provider, a pneumatic or hydraulic device, such as a syringe pump, may be used. As the pressure provider controls the flow rates within the channel, the antibody is allowed to effectively react with the tissue sample. As for the driving force behind the fluid flow, it may be obtained from the pump 152 connected with a fluid outlet 151 or may be the result of direct pressure applied to the antibody loading unit. Alternatively, an antibody alone may be loaded to the antibody-loading unit so as to react with a sample present underneath it, without applying direct pressure to the antibody-loading unit.

In the multiple immunoassay apparatus in accordance with a first embodiment of the present invention, as described above, antibodies are loaded onto the antibody-loading units 111~118 and flow into the reaction units 131~138 under the cooperative control of the pressure provider and the fluid controller where they are subjected to multiple immune reactions with a sample 141 including tissues samples, cells and the like, followed by discharge via the fluid outlet 151. Preferably, each of the reaction units is 3 cm or smaller in width because widths of tissue samples generally do not exceed 3 cm and many reaction units are provided for multiple immunoassays. Further, the multiple immunoassay apparatus in accordance with the present invention may be prepared in the structure of a lab-on-a-chip, ensuring the simple and effective implementation of immunoassays.

The structure and assemblage of the multiple immunoassay apparatus in accordance with the present invention is useful in understanding the operation thereof. With reference to FIG. 2, a sample 141 placed on a lower assembly plate 200 is assembled with the apparatus of FIG. 1 which is associated with a compression plate 400 and an upper assembly plate 500. Here, the apparatus is preferably assembled with the sample in such a manner that a fluid, such as a blocking solution, is positioned on the sample. When the apparatus is correctly assembled, the first to the eighth antibodies are introduced through the antibody loading units 111~118, respectively. Although eight antibody loading units are provided in this embodiment, the number may vary depending on requirements or designs. In the reaction units 131~138 which are respectively connected via channels to the antibody loading units, antibodies, after migrating thereto via the channels, interact with tissue samples. A pressurizing unit 600 is provided for pressurizing the reaction units to effectively carry the antibody to the reaction units, thus leading to sufficient reaction between the reagents, the antibodies and the samples. The pressurizing unit 600 is operated using a bolt-nut joint, a balance weight, or a spring compressor.

Also, the apparatus may further comprise a pressure provider, connected to both the antibody loading unit and the reaction unit, for controlling the flow rate of the fluid within the channel. As an example of the pressure provider, a syringe pump is connected to the fluid outlet 151, generating a vacuum to allow the antibodies to flow toward the reaction units and to react with samples in the reaction units. After completion of the reaction, the pressurizing unit is loosened to separate the compression plate and the upper assembly plate from the sample. Then, the sample may undergo typical processing following the primary antibody reaction.

Through the fluid outlet 151, fluids including antibodies which remain unbound to the sample are discharged. As described above, a pressure provider, such as a device for generating a vacuum, like a syringe pump, may be applied to the fluid outlet to help the discharge of the fluid.

In addition, the apparatus may further comprise an electric heater 800 for controlling a temperature to promote the reaction. Located on the bottom surface of the apparatus, the electric heater functions to maintain a temperature at which optimal reactivity can occur. For fluorescence in situ hybridization (FISH), the electric heater can achieve a suitable temperature. Also, cells may be cultured in a vessel adaptable to the channel of the reaction unit. Thus, the researcher can conducted desired molecular biological or cell biological experiments without limitations as to the apparatus. Grooves, although not shown, are formed at the verge of a sample support on the lower plate 200 to contain liquid such as water therein, thereby preventing the evaporation of the reagents and antibodies introduced into the multiple immunoassay apparatus. This can reduce the consumption of expensive antibodies.

Second Embodiment

Figure 3:
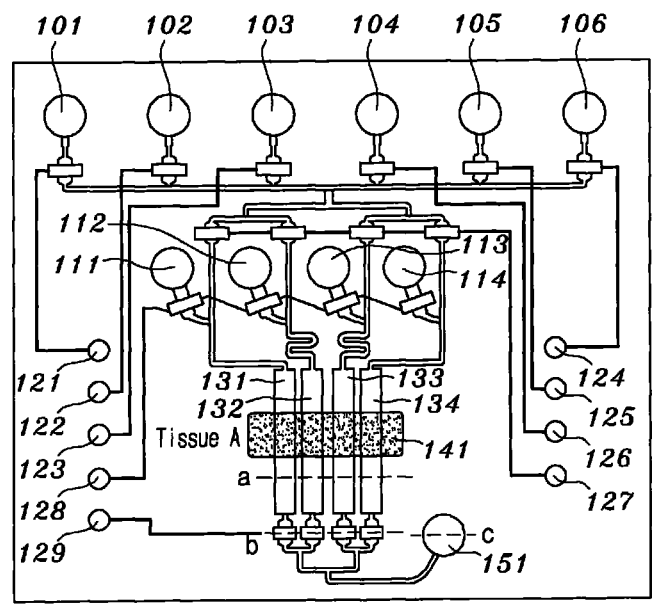
FIG. 3 is a structural view of a multiple immunoassay apparatus in accordance with a second embodiment of the present invention.
Figure 4:
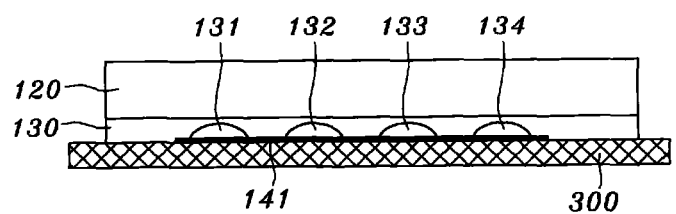
FIGS. 4 to 6 are cross-sectional views of the multiple immunoassay apparatus of FIG. 3.
Figure 5:
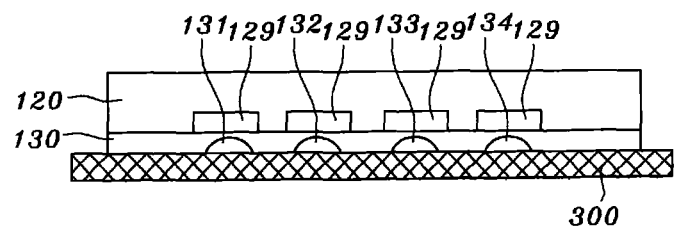
Figure 6:
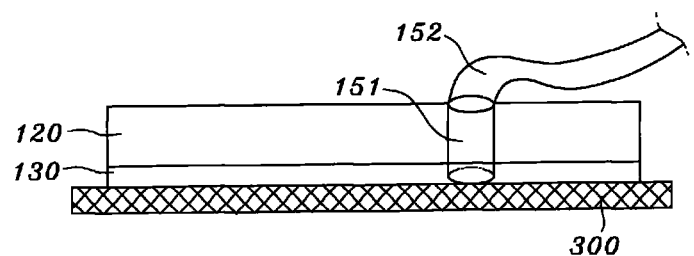

Referring to FIG. 3, a multiple immunoassay apparatus on a chip in accordance with a second embodiment of the present invention is shown. As shown, the multiple immunoassay apparatus on a chip in accordance with the second embodiment of the present invention further comprises a reagent introducing unit through which a reagent necessary for immunohistochemistry is introduced into the apparatus. In this example, a first reagent introducing unit 101 to a sixth reagent introducing unit 106 are provided. For instance, the first reagent introducing unit 101 may be provided for TBS Tween washing buffer, the second reagent introducing unit 102 for a biotinylated secondary antibody, the third introducing reagent unit 103 for streptavidin-HRP, the fourth reagent introducing unit 104 for distilled water, the fifth reagent introducing unit 105 for DAB, and the sixth reagent introducing unit 106 for Mayer's hematoxylin. The number of reagent introducing units may be increased or decreased according to the number of required reagents.

Various reagents necessary for biological experimentation, such as those necessary for immunohistochemistry, can be, thus, readily introduced through the reagent introducing units of the present invention. The reagent introducing units are connected with respective fluid controllers 121~126 for controlling flow rates of the reagents.

There are as many antibody loading units, communicating with both the reaction units and the reagent introducing units, as there are channels of the reaction units. Each of the antibody loading units is also provided with a fluid controller 128 for controlling the flow rate of the antibodies. The antibody loading units may vary in number as well, depending on requirements. In the same manner as in the First Embodiment, fluids in the reagent introducing units, the antibody loading units and the channels are controlled by the fluid controllers 121~129. That is, the fluid controllers are connected to the reagent introducing units, the antibody loading units, the reaction units and the fluid outlet, respectively, and control the flow rates of many fluids.

As in the first Embodiment, the apparatus comprises a pressure provider, connected to the channel, for providing pressure to control the flow rate of the fluid within the channel. As the pressure provider, a pneumatic or hydraulic device, such as a syringe pump, may be used. Under the control of flow rates within the channel by the pressure provider, the antibody is allowed to effectively react with the tissue sample. As for the driving force for the fluid flow, it may be obtained from the pump connected with a fluid outlet 151 or may result from direct pressure applied to the antibody loading unit. The number of the fluid controllers connected via valves respectively to the fluid channels may be increased or decreased depending on the number of both the reagent introducing units and the antibody loading units.

In the reaction units which are respectively connected via the channels to the antibody loading units, antibodies, after migrating thereto via the channels, interact with tissue samples. A pressurizing unit 600 is provided for pressurizing the reaction units to effectively carry the antibody to the reaction units, thus leading to sufficient reaction between the reagents, the antibodies and the samples. The pressurizing unit 600 is operated using a bolt-nut joint, a balance weight, or a spring compressor.

The tissue samples reactive to the antibodies include tissues and cells. For the convenience of binding between the antibodies and the tissue samples, an assembler may be provided. Different reagents may be introduced into the reaction units via the channels, allowing the simultaneous implementation of various experiments.

Through the fluid outlet 151, fluids including reagents and unbound antibodies are discharged. The fluid outlet 151 may be connected with a pressure provider via a tube 152. In this regard, the tube may be applied to the fluid outlet at any time during the above-mentioned procedure. A representative example of the pressure provider includes a syringe pump.

Figure 7:
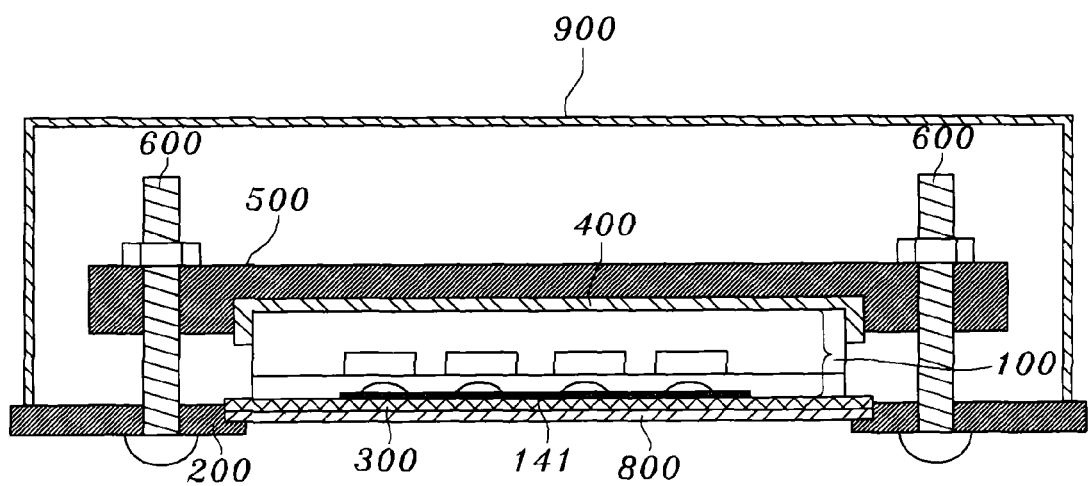
FIG. 7 is a cross-sectional view of the multiple immunoassay apparatus in accordance with the second embodiment of the present invention, covered with a cover.

An application of a cover 900 to the apparatus according to the Second Embodiment is shown in FIG. 7. The cover, made of a transparent material, prevents the evaporation of the fluids used in the apparatus, allowing the view of the immune responses therethrough. In addition to the cover 900, the sample support 300, the compression plate 400 and the upper assembly plate are preferably made of transparent materials for the convenience of microscopic observation. Also, the upper assembly plate has openings for channels of the multiple immunoassay apparatus, for example, at positions for the reagent introducing units, the fluid controllers, the antibody loading units and the fluid outlet. No explanations are given of the other constituents because they are the same as in the Second Embodiment.

Third Embodiment

Figure 8:
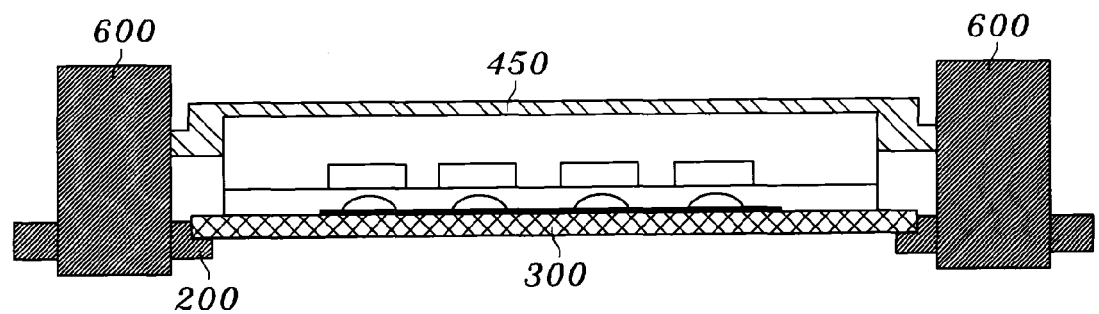
FIG. 8 is a cross-sectional view of a multiple immunoassay apparatus in accordance with a third embodiment of the present invention.

FIG. 8 is a cross sectional view of a multiple immunoassay apparatus in accordance with a third embodiment of the present invention. This apparatus, as described above, comprises a compression plate-incorporated upper assembly plate 450 having openings for the reagent introducing units, the fluid controllers, the antibody loading units and the fluid outlet, which is arranged with the lower assembly plate. In this embodiment, the upper assembly plate and the compression plate are integrated into one plate so that the apparatus is more simple in organization and can be more easily assembled.

Fourth Embodiment

Figure 9:
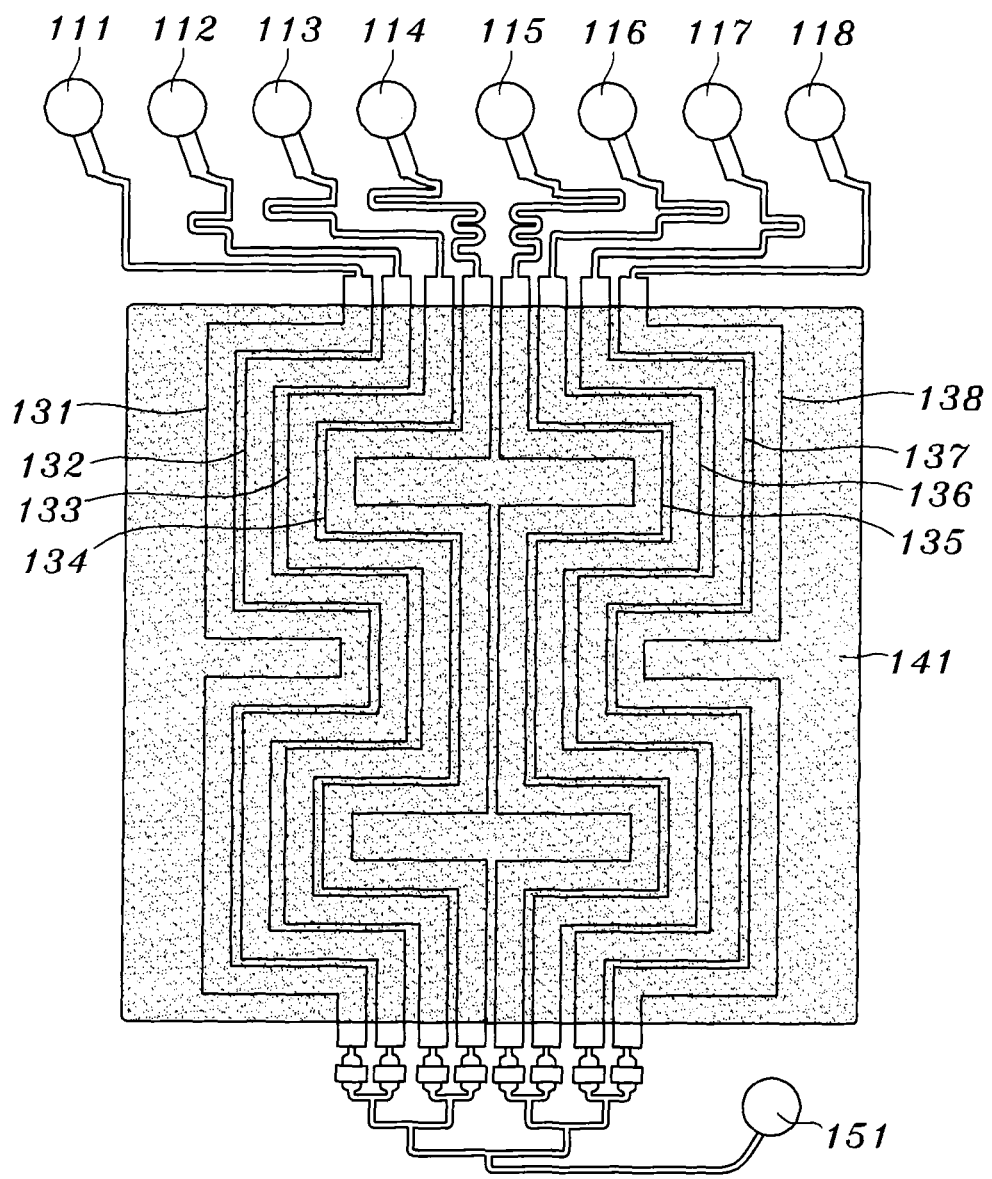
FIG. 9 is a structural view of a multiple immunoassay apparatus in accordance with a fourth embodiment of the present invention.
Figure 11:
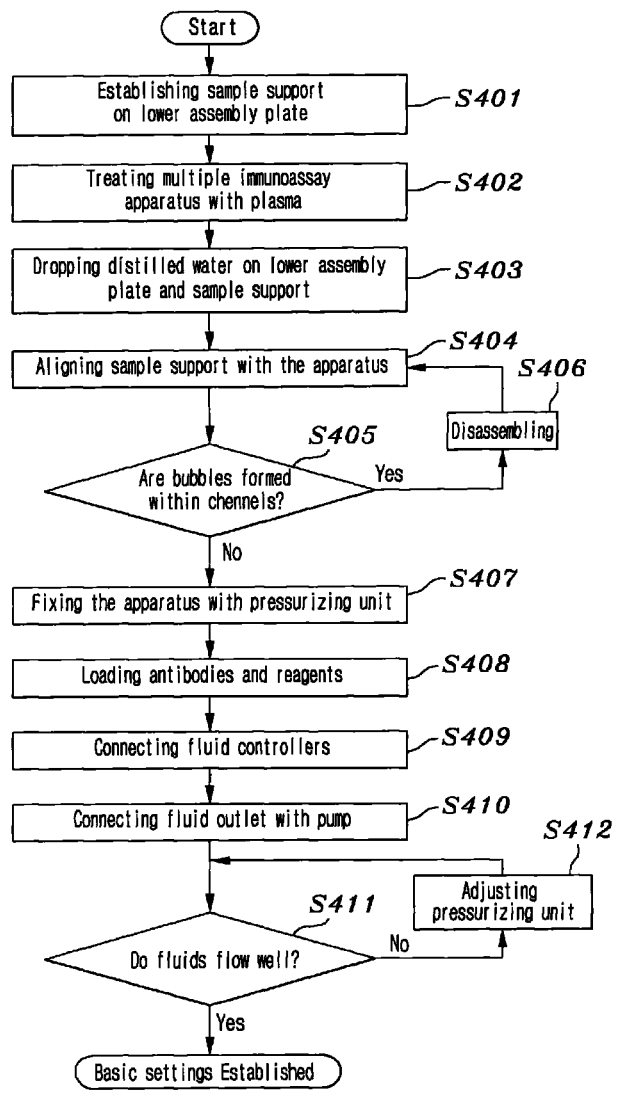
FIG. 11 is a flow chart showing the setting process of the multiple immunoassay apparatus.

FIG. 9 shows an apparatus according to a fourth embodiment of the present invention. In contrast to the straight reaction units of FIGS. 1 and 2, the reaction units of this embodiment are in zigzag form which ensures larger areas for the reaction between the samples and the antibodies to improve the reliability of the immunoassays. Although the reaction units are shown in the form of zigzags symmetric with respect to the center, it should be understood that various forms may be applied to the entirety of reaction units in order to achieve the above-mentioned intention, that is, to increase the area of the entire reaction units. The apparatus of FIG. 11 is identical in operation and order to that of FIG. 1 or 2.

Fifth Embodiment

Figure 10:
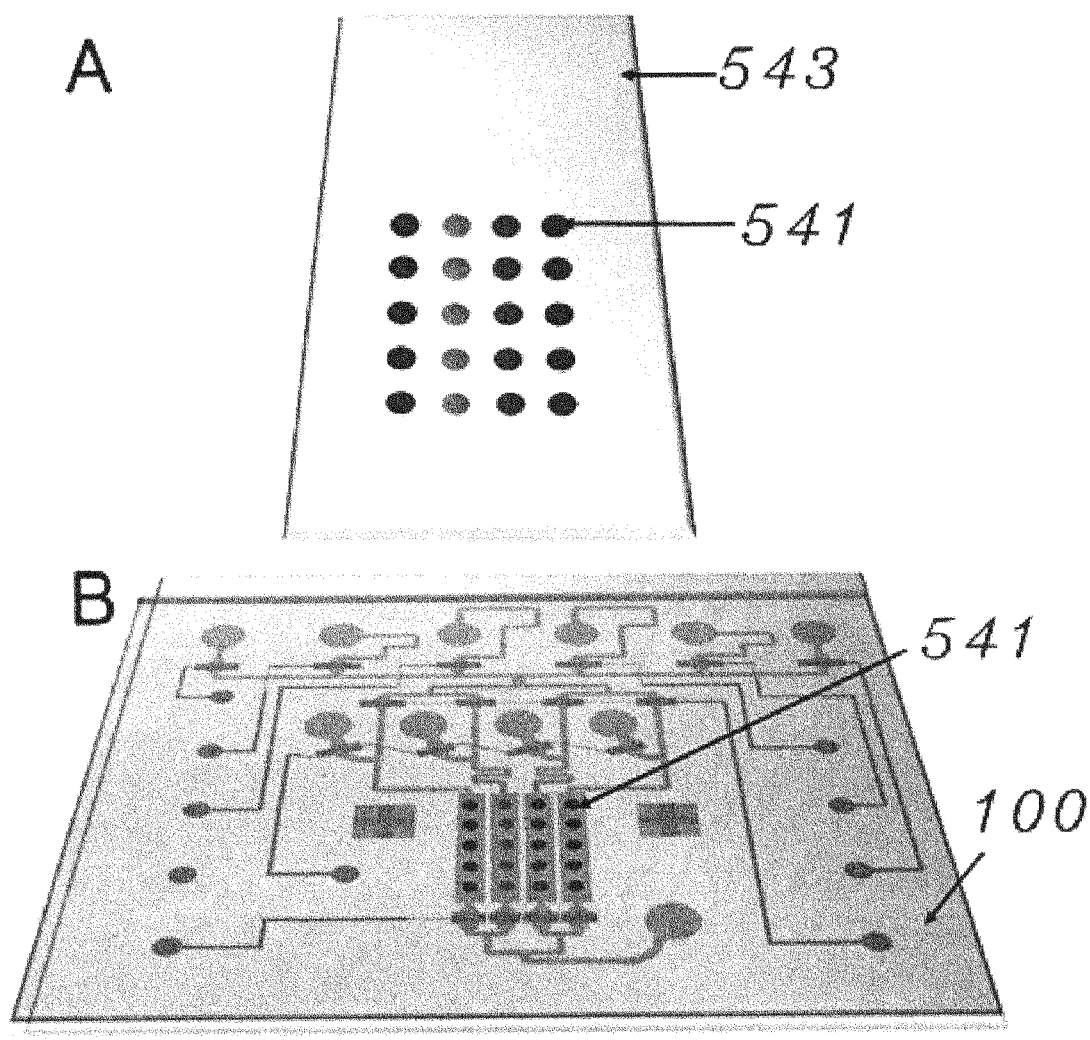
FIG. 10 is a structural view of a multiple immunoassay apparatus in accordance with a fifth embodiment of the present invention.

FIG. 10 shows an application of the multiple immunoassay apparatus of the present invention to a tissue microarray 541. In this embodiment, as shown in FIG. 10, tissue samples are arranged in the form of an array on a slide glass 543 and are overlaid with the multiple immunoassay apparatus to give a system in which various tissue samples can be monitored for immune responses to various antibodies. In this figure, the arrayed tissue samples are depicted as smaller than the channels of the reaction units of the multiple immunoassay apparatus. However, if the tissue samples are prepared in a size larger than the total width of the reaction units, each of various tissue samples can be assayed for reactions with various antibodies. In order to achieve this, the reaction unit channels of the multiple immunoassay apparatus in accordance with the present invention must be fabricated into an array form which is lined with the tissue samples placed on the slide glass. It should be noted that this organization is included within the scope of the present invention.

Next, a brief explanation is given of the assay method using the multiple immunoassay apparatus. First, a tissue slice to be inspected is placed on a sample support, such as a slide glass, followed by positioning the multiple immunoassay apparatus of FIG. 1 or 3 thereover, In this regard, the reaction units of the multiple immunoassay apparatus are aligned with the tissue sample at the position 141 to be inspected. It is very important to correctly align the reaction units with the sample located underneath. After the alignment, reagents and antibodies are loaded into the reagent introducing units and antibody loading units respectively. A pump connected to the fluid outlet is operated to flow the fluids at suitable flow rates, for example, at a flow rate of 50 μl/h.

The application of the apparatus of the present invention to immunohistochemistry enjoys the advantage of obtaining information on the reaction of various antibodies with one tissue sample. If the fluid controller 128 is open while the other valves 121~127 and 129 are closed, four different antibodies 111~114 are allowed to flow towards the four reaction channels 131~134, respectively and react with a sample in the respective reaction units. In order to maintain the reaction of the sample with the antibodies, they may be allowed to slowly flow or may be confined within the reaction units by closing the fluid controller 129.

After completion of the immune responses, reagents may be allowed to flow to the reaction units according to immunohistochemical procedures. For example, when the valves 121, 127 and 129 are open while the other valves 122, 123, 124, 125, 126 and 128 are closed, TBS Tween washing buffer loaded to the first reagent introducing unit flows through the four reaction channels. In a manner similar to this, the other reagents can be allowed to flow through the channels. As each channel is being used it may be observed under a microscope to examine the reaction of the sample. The images thus obtained may be analyzed in a subsequent process. Alternatively, the sample support is separated from the multiple immunoassay apparatus after the completion of the reaction, and observed under a microscope. Also, the sample support may be stored separately. The above-described setting and examination processes of the apparatus are summarized in the flow charts of FIGS. 11 and 12.

FIG. 11 is a flow chart showing the setting process of the multiple immunoassay apparatus.

First, a lower assembly plate is prepared. A sample support is placed on the lower assembly plate (S401). The multiple immunoassay apparatus, after being positioned over the sample support, is treated with plasma (S402) and distilled water is dropped on the lower assembly plate and the sample support (S403) before the alignment of the apparatus with the sample support (S404). Thereafter, an examination is made of the occurrence of bubbles between the sample support and the apparatus (S405). When bubbles are formed between the sample support and the apparatus, they are disassembled (S406). Then, the multiple immunoassay apparatus is aligned with the sample support lest bubbles should be formed (S404). Upon the reformation of bubbles, the realignment of the sample support with the apparatus is repeated until the bubbles are not formed.

When no bubbles are formed after the alignment of the sample support with the multiple immunoassay apparatus, an upper assembly plate is laid on the apparatus and fixed to the lower assembly plate with a pressurizing unit for compressing the apparatus (S407). After the compression of the tissue sample and the multiple immunoassay apparatus, reagents and antibodies are loaded into the reagent introducing units and the antibody loading units, respectively (S408). In order to allow the reagents and the antibodies to flow well, the fluid controllers communicating with the reagent introducing units, the antibody loading units and the fluid outlet are connected with each other (S409). The fluid outlet, extending through channels to the reaction units, is connected via a tube to a pump for generating a vacuum to promote the flow of the fluids through the reaction units (S410).

Subsequently, an examination is made of whether the fluids are flowing well through channels (S411). If the fluids are not flowing or the fluid controllers are not operated appropriately, the pressurizing unit for compressing the apparatus and the tissue sample is controlled such that the fluids flow well or that the fluid controllers are operated well (S412). Therefore, if the fluids flow well and the fluid controllers function well, basic settings are said to be established.

Figure 12:
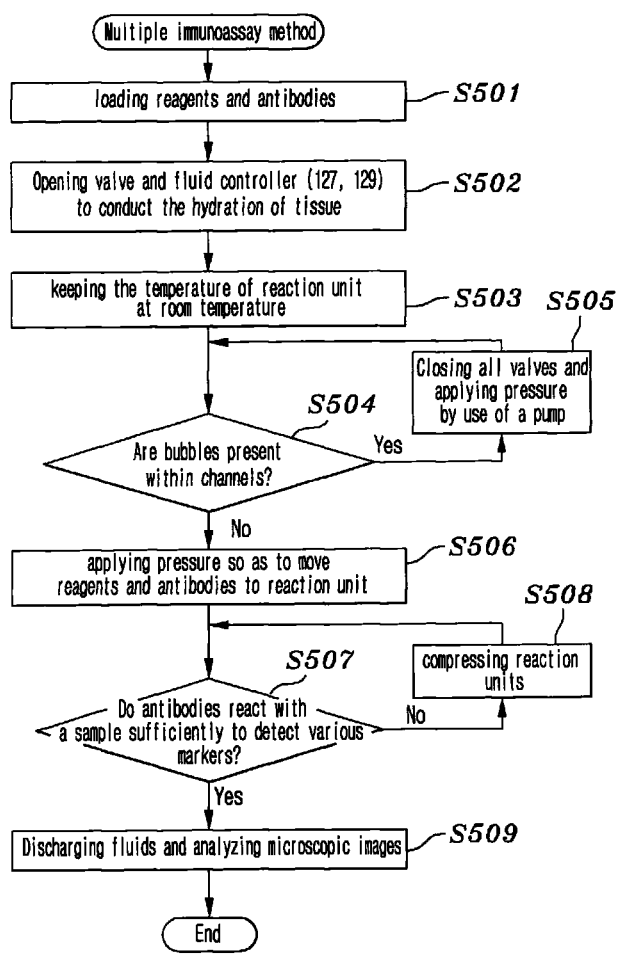
FIG. 12 is a flow chart showing a multiple immunoassay method.

With reference to FIG. 12, an immunoassay method is illustrated in a flow chart.

First, at least one reagent and at least one antibody are loaded into the reagent introducing unit and the antibody loading unit, respectively (S501). Next, the following measures are taken, before reactions with tissue samples, in order to establish optimal conditions for the reactions.

Valves 127 and 129 for the fluid controllers containing a deparaffinized solution are opened after which a 100% ethanol valve, a 95% ethanol valve, a 80% ethanol valve, a 70% ethanol valve and a distilled water valve are opened in that order, to conduct the hydration of the tissue (S502). While the electric heater located at a lower side of the sample support supporting the apparatus is set at 90° C., a valve containing citrate buffer or TRIS-EDTA buffer is opened. The electric heater is turned off to keep the temperature of the reaction unit at room temperature, which is optimal for reactions between the antibodies and the tissue sample (S503).

After an optimal condition for the reactions is maintained, the presence of bubbles inside the channels is examined (S504). Bubbles within the channels inhibit the reactions. When bubbles are observed within the channels, all of the open valves are closed and the bubbles are removed from the channel by applying a pressure through the pump connected to the fluid outlet via the tube (S505). A representative example of this pump includes a syringe pump. This procedure is repeated until no bubbles are being formed.

If no bubbles are present inside the channels, a hydrogen peroxide valve, a TBS Tween buffer valve, and a Blocking solution valve are opened sequentially in that order while the fluid controller valve 127 is closed.

After the completion of the washing and temperature control, a pressure is applied so as to move the reagents and the antibodies to the reaction units (S506). If the antibodies are not completely moved to the reaction units, a vacuum is applied through the pump to fill the reaction units with the antibodies.

When moved to the reaction units, the antibodies react with the tissue sample so that various markers can be detected (S507). At this time, the reaction units may be pressurized to promote this reaction (S508). After completion of the reaction, a TBS Tween buffer valve, a Streptavidin HRP valve, and a distilled water valve are sequentially opened in that order, followed by opening a DAB valve, a distilled water valve and a Mayer's Hematoxylin valve and then a distilled water valve, an ethanol valve and a Xyline valve. In this state, microscopic images are obtained and analyzed. Thereafter, the fluids including the reagents and antibodies are discharged through the fluid outlet connected to the reaction units (S509). Through these processes, the multiple immunoassays are completed.

Figure 13:
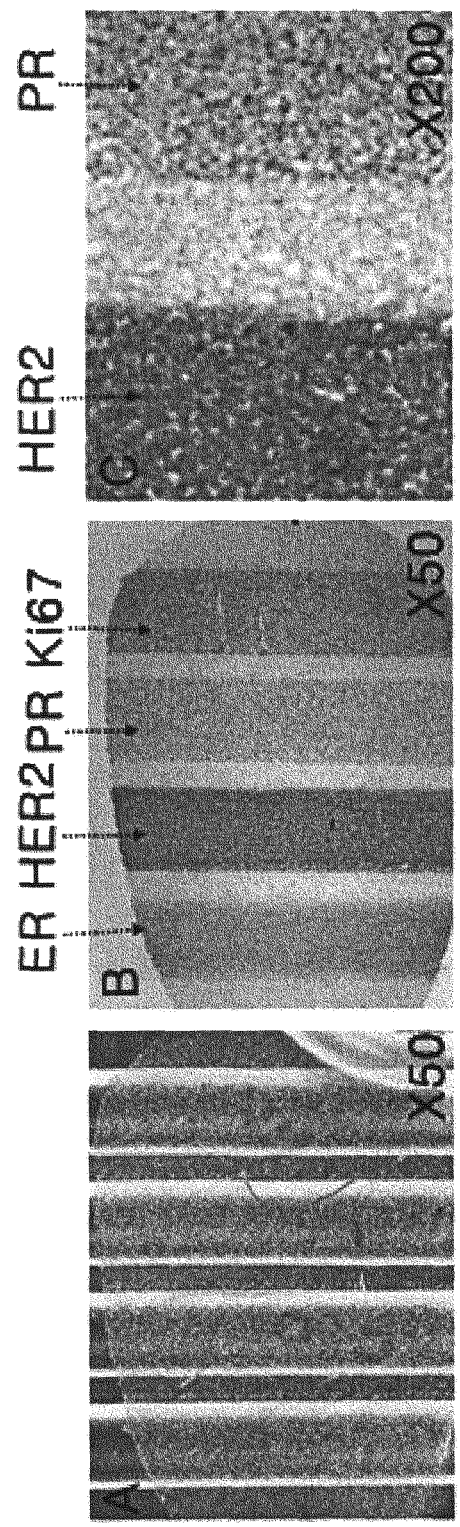
FIG. 13 shows one cellblock sample which is immunoassayed with various antibodies using the multiple immunoassay apparatus of the present invention.

FIG. 13 shows one cellblock sample which is immunoassayed with various antibodies using the multiple immunoassay apparatus of the present invention. FIG. 13A is a view of a sample (breast cancer cell line: AU-565) on which the multiple immunoassay apparatus is placed. Immunohistochemical results of the sample with respect to antibodies to estrogen receptor, HER2, progesterone receptor and Ki67 are shown in FIG. 13B. As seen in FIG. 13C, responses to various antibodies can be achieved on one sample with distinct immunohistochemical results.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

Capable of obtaining extensive information on the prognosis of patients, the apparatus and method of the present invention is greatly helpful in choosing therapeutic methods and reduces biochemical and medical examinations in terms of time and cost, thus allowing medical treatments to be rapidly applied to patients with a great reduction in financial burden of the patients.

The invention claimed is:

1. An assembly comprising a multiple immunoassay apparatus and a sample, wherein the multiple immunoassay apparatus comprises:
   (a) at least two antibody-introducing units, wherein each antibody-introducing unit introduces a respective antibody into the apparatus;
   (b) at least two microchannels, through each of which a fluid containing said respective antibody flows, wherein each microchannel is connected to each antibody-introducing unit;
   (c) at least two reaction units in which the antibody reacts with the sample in an immunohistochemical pattern wherein each reaction unit is formed from a portion of the respective microchannel, each reaction unit contacts the sample, and each reaction unit comprises an open part toward the sample such that when the fluid containing a respective antibody flows through the microchannel between the reaction unit and the sample, the fluid contacts a portion of the sample via the open part and an immune reaction take place in each reaction unit;
   (d) at least one fluid outlet through which the fluid containing the respective antibody is discharged outside the apparatus from the reaction units; and
   (e) a pressurizing unit that compresses the reaction unit toward the sample;
   wherein the sample is one piece of tissue.

2. The assembly according to claim 1, further comprising a pressure provider for providing pressure to control a flow rate of fluid within the at least two microchannels.

3. The assembly according to claim 2, wherein the pressure provider is a hydraulic or pneumatic device.

4. The assembly according to claim 1, further comprising an electric heater for controlling a temperature of the apparatus, wherein said electric heater being located on a lower side of the apparatus to establish a condition optimal for a reaction between the antibody and the sample.

5. The assembly according to claim 1, wherein there are as many reaction units as antibody-introducing units.

6. The assembly according to claim 1, further comprising a transparent cover for covering the apparatus to prevent the fluid from evaporating.

7. The assembly according to claim 1, further comprising at least one reagent-introducing unit through which a reagent necessary for an immunoassay is introduced.

8. The assembly according to claim 1, wherein the pressurizing unit is operated in a bolt-nut manner, a spring compressing manner, or a balance weight manner.

9. The assembly according to claim 1, wherein the reaction units are formed in a zigzag pattern.

10. The multiple immunoassay apparatus assembly according to claim 7, wherein the antibody and the reagent are reacted with the sample while flowing through the reaction unit.

11. The assembly according to claim 7, having a lab-on-a-chip structure in which the antibody-introducing units, the reagent-introducing units, the reaction units and the fluid outlet are all established on a chip.

12. A method for performing multiple immunoassays using the assembly according to claim 1, comprising:

loading the respective antibody into the respective antibody-introducing unit;

providing pressure to move each fluid containing the respective antibody to the respective reaction unit;

allowing the antibodies to react with the sample to examine markers specific for diseases; and discharging the fluids through the fluid outlet connected to the reaction units.

13. The method according to claim 12, further comprising loading a reagent into a respective reagent-introducing unit prior to, subsequently to or simultaneously with the loading of the respective antibody.

14. The method according to claim 12, further comprising controlling flows of the fluids including the antibodies and the reagents to the sample after the provision of pressure.

15. The method according to claim 12, wherein the pressure is provided using a hydraulic or pneumatic device.

16. The method according to claim 12, further comprising compressing the reaction units to promote the reaction between the antibodies and the sample.

17. The method according to claim 13, further comprising controlling flows of the fluids including the antibodies and the reagents to the sample after the provision of pressure.

* * * * *